(12) United States Patent
Traving et al.

(10) Patent No.: US 7,393,969 B2
(45) Date of Patent: Jul. 1, 2008

(54) PARTICULAR CALIXARENES METHOD FOR PRODUCTION AND USE THEREOF

(75) Inventors: Michael Traving, Burscheid (DE);
Wilfried Gutknecht, Goslar (DE);
Werner Bäcker, Wipperfürth (DE);
Wolfgang Kummer, Goslar (DE);
Rainer Ludwig, Berlin (DE)

(73) Assignee: Bayer Technology Services GmbH, Leverkusen (DE)

( * ) Notice: Subject to any disclaimer, the term of this patent is extended or adjusted under 35 U.S.C. 154(b) by 0 days.

(21) Appl. No.: 11/574,144

(22) PCT Filed: Aug. 16, 2005

(86) PCT No.: PCT/EP2005/008865

§ 371 (c)(1),
(2), (4) Date: May 8, 2007

(87) PCT Pub. No.: WO2006/021342

PCT Pub. Date: Mar. 2, 2006

(65) Prior Publication Data

US 2007/0232826 A1    Oct. 4, 2007

(30) Foreign Application Priority Data

Aug. 24, 2004   (DE) .................. 10 2004 040 923

(51) Int. Cl.
*C07C 69/76* (2006.01)
*B01D 15/00* (2006.01)
(52) U.S. Cl. ...................... 560/57; 210/660; 210/662
(58) Field of Classification Search .................. None
See application file for complete search history.

(56) References Cited

U.S. PATENT DOCUMENTS

| 4,556,700 A | * | 12/1985 | Harris et al. | 526/209 |
| 5,132,345 A | * | 7/1992 | Harris et al. | 524/108 |
| 6,576,192 B1 | * | 6/2003 | Waldner et al. | 422/56 |

FOREIGN PATENT DOCUMENTS

| EP | 0 237 265 A | 9/1987 |
| EP | 0 490 631 A | 6/1992 |

OTHER PUBLICATIONS

Galan-Mascaros et al; "A novel chainlike heteropolyanion fromed by keggin units: synthesis and structure of (ET) 8n[PMnW11O39]n . 2nH2O**"; Angew. Chem. Int. Ed. Engl. 34, No. 13, 1995, pp. 1460-1462.
Grady, T. et al; "Determination of the enatiomeric composition of chiral amines based on the quenching of the fluorescence of a chiral calixarene"; Anal. Chem. vol. 68, No. 21 (1996) pp. 3775-3782 XP002364286.
Diamond, D. et al.; "Characteristics of sodium-selective electrodes based on a triethylester monoacid derivative of p-tert-Butylcalix'4'arene"; Analytical Proceedings, vol. 32, No. 4 (1995) pp. 137-140 XP009060386.
Barrett, G. et al; "Selective monohydrolysis of bridged and unbridged calix'4'arene esters and its inhibition by alkali ion. Evidence for hydronium ion complexation"; J. Chem. Soc. Perkin Trans. 2, vol. 9 (1992) pp. 1595-1601 XP009060359.
Ludwig, R. et al; "New macrocyclic extractants for the processing of inorganic waste"; Nukleonik, vol. 32, No. 2 (1998) pp. 161-173 XP009060384.
Chawla, H.M. et al.; "Synthesis of 25,26,27-Tris(ethoxycarbonylmethoxy)-28-(4-methyl-7-coumarinyloxycarbonylmethoxy)calix-4-arene"; Indian Journal of Chemistry, vol. 32B (1993) pp. 1162-1164 XP009060385.
Arnaud-Neu, F. et al.; "Selective alkali-metal cation complexation by chemically modified calixarenes. Part 4. Effect of substituent variation on the Na+/K+ selectivity in the ester series and X-ray crystal structure of the trifluoroethyl ester"; J. Chem. Soc. Perkin Trans. 2, vol. 7 (1992) pp. 1119-1125 XP009060397.
Groenen L.C. et al.: "Syn-1,2-Dialkylated calix'4'arenes: General intermediates in the NaH/DMF tetraalkylation of calix'4'arenes" Tetrahedron Letters, vol. 32, No. 23 (1991) pp. 2675-2678 XP002364287.
Iwamoto, K. et al.: "Remarkable metal template effects on selective synthesis of p-t-butylcalix'4'arene conformers"; Tetrahedron Letters, vol. 31, No. 49 (1990) pp. 7169-7172 XP002364288.
Iwamoto, K. et al.; "Conformations and structures of tetra-O-alky-p-tert-butylcalix'4'arenes. How is the conformation of calix'4'arenes immobilized?" J. Org. Chem., vol. 56 (1991) pp. 4955-4962 XP002364289.
Inokuchi, F. et al.; "Selektive Erkennung Von Alkalimetall-Kationen durch pi-basische, molekulare Hohlraume und einfacher massenspektrometrischer Nachweis von Kation-Aren-Komplexen"; Angew. Chem., vol. 107, No. 12 (1995) pp. 1459-1462 XP009060511.

* cited by examiner

*Primary Examiner*—Paul A Zucker
(74) *Attorney, Agent, or Firm*—Norris McLaughlin & Marcus PA

(57) ABSTRACT

The present invention relates to calix[4]arenes which effectively bind alkali metal ions (Na$^+$, K$^+$) and transport them over phase boundaries, their preparation and use.

8 Claims, 2 Drawing Sheets

PARTICULAR CALIXARENES METHOD FOR PRODUCTION AND USE THEREOF

This application is a 371 of PCT/EP2005/008865, filed Aug. 16, 2005, which claims foreign priority benefit under 35 U.S.C. § 119 of the German Patent Application No. 10 2004 040 923.4 filed Aug. 24, 2004.

The present invention relates to calix[4]arenes which effectively bind alkali metal ions (Na$^+$, K$^+$) and transport them over phase boundaries, their preparation and use.

The selective removal of alkali metal ions can improve product quality in the metal-producing industry, the polymer industry, the biotechnological industry and other industries by making it possible to achieve a higher purity and, associated therewith, new and improved materials properties in the product. In such separations, acidic or basic digestion solutions whose pH is to remain unchanged are frequently present. For this reason, neither acids nor bases (ammonia, inter alia) should be separated off if possible.

Calix[4]arenes are calix[n]arenes in which n=4 benzene rings are bridged to one another. (Gutsche (1998) *Calixarenes Revisited*, The Royal Society of Chemistry, Cambridge, UK; Ludwig (2000) Fresenius' J. Analyt. Chem., 367(2), 103-128). As a result of substitution reactions on the molecular skeleton, numerous derivatives are known. Some of these derivatives display selectivity toward metal ions, e.g. Pb(II), Au(III), Ln(III) or Am(III). This selectivity can be utilized for chemical separations. The present patent text describes calix[4]arenes whose molecular structure has been altered so that the alkali metal ions Na$^+$ and K$^+$ can be removed selectively even from strongly ammoniacal solutions by means of liquid-liquid extraction, adsorption or membrane techniques, leaving other metal ions completely in solution. We have surprisingly found that this object can be achieved, inter alia, by means of calixarenes which do not bear any crown ether groups, as has been the case in developments hitherto, which are summarized below.

The chemical removal of alkali metal ions Na$^+$ and K$^+$ is, because of their very low tendency to form complexes (Powell (2000) The IUPAC Stability Constants Database, Academic Software), one of the most difficult separation problems there is in chemistry. The first successful approach to a solution was with use of crown ethers (Pedersen (1970) J. Amer. Chem. Soc., 92(2), 391-394; Strzelbicki & Bartsch (1981) Analyt. Chem., 53(12), 1894-1899; Hayashita, Goo, Lee, Kim, Krzykawski, & Bartsch (1990) Analyt. Chem., 62(21), 2283-2287; Bartsch, Hayashita, Lee, Kim, & Hankins (1993) Supramol. Chem., 1, 305-311; Bartsch & Hayashita (1999) ACS Symposium Series 716: Metal-Ion Separation and Preconcentration; Lindner, Toth, Jeney, Horvath, Pungor, Bitter, et al. (1990) Mikrochim. Acta [Vienna], 1, 157-168; Imato, Honkawa, Kocsis, & Imasaka (1993) Proc. of the East Asia Conference on Chemical Sensors, 268-271; Bereczki, Agai, & Bitter (2003) J. Inclusion Phen. and Macrocyclic Chem., 47, 53-58; Izatt, Pawlak, Bradshaw, & Bruening (1991) Chem. Rev., 91(8), 1721-2085).

However, crown ethers are unsuitable for industrial applications since, for example, (i) they penetrate into the skin on contact and lead to death of the skin, (ii) are somewhat water-soluble and thus relatively unsuitable for a continuous process and (iii) are very expensive. This class of compounds has therefore found some degree of use only in the chemical-analytic and chemical-preparative field.

All known techniques therefore lead to unsatisfactory results in respect of the selective removal of alkali metal ions or to high costs associated therewith.

Calixarenes are in principle able to avoid the three disadvantages mentioned. To give a calixarene a selectivity for Na$^+$ among the group of alkali metal ions which is sufficiently high for practical applications, crown ether groups have hitherto been integrated into the molecule (Beer, Drew, Knubley, & Ogden (1995) J. Chem. Soc. Dalton Trans. (19), 3117-3124; Koh, Araki, Shinkai, Asfari, & Vicens (1995) Tetr. Lett., 36(34), 6095-6098; Scheerder, Duynhoven, Engbersen, & Reinhoudt (1996) Angew Chemie, 108(10), 1172-1175; Shibutani, Yoshinaga, Yakabe, Shono, & Tanaka (1994) J. Inclusion Phen. and Molec. Recognition in Chem., 19, 333-342; Yamamoto, Sakaki, & Shinkai (1994) Chem. Letters (3), 469-472; Yamamoto & Shinkai (1994) Chem. Letters (6), 1115-1118; Yamamoto, Ueda, Suenaga, Sakaki, & Shinkai (1996) Chem. Letters, 39-40).

Some of these molecular structures have been patented, with application being in the analytical field (Yamamoto & Ogata (1992) JP 04339251, 16 Nov.; Yamamoto & Shinkai (1994) JP 07206852, 8, Aug. 1995; Yamamoto (1995) JP Appl. H7-79787, 10. March; Yamamoto, Sakaki, & Shinkai (1995) JP 08291165, 5, Nov. 1996; Yamamoto & Shinkai (1996) JP 08245616, 24. 9.).

The crown ether group has the following functions in the molecule (i) a stiffening of the structure so that the functional groups are kept in a defined, barely changeable position in space and (ii) to form a hollow space of particular size. If the crown ether group or a similar group such as an aza crown ether group is extended, the ligand becomes selectively for K$^+$ (Casnati, Pochini, Ungaro, Bocchi, Ugozzoli, Egberink, et al. (1996) Chem. Europ. J., 2(4), 436-445; Kim, Shon, Ko, Cho, Yu, & Vicens (2000) J. Org. Chem., 65(8), 2386-2392; Shinkai (1994) JP6116261, 26.4.; Wenger, Asfari, & Vicens (1995) J. Inclusion Phen. and Molec. Recognition in Chem., 20, 293-296).

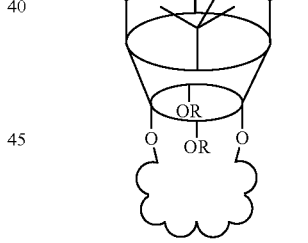

(1) Schematic depiction of a crowned calixarene having the calix[4]arene skeleton, a group R=H forming a hollow space or further substituents and a bridging crown ether ring, e.g.— (OCH$_2$CH$_2$—)$_n$ This structural approach using crown ether groups (1) can also be employed for preparing Cs$^+$-selective calixarenes (Dozol, Asfari, Hill, Vicens (1994) FR 2698362, 27, May; Dozol, Rouquette, Ungaro, & Casnati (1994) WO9424138, 20, Jul. 1999; Moyer, Sachleben, Bonnesen, Presley (1999) WO 9912878, 18, March). This group of substances, also known as crowned calixarenes, is nontoxic and insoluble in water. However, their synthesis is complicated since (i) the stepwise preparation of the crown ether group having a defined length is complicated and therefore expensive, (ii) the reaction yield is low because of a plurality of possible reaction paths (bridge formation, substitution without bridge formation) and (iii) a complicated purification by means of chromatography or phase transfer is necessary because of the unbridged by-products. Although crowned calixarenes have the highest known selectivities for alkali metal ions, they have for these reasons hitherto only been used in analytical methods or in specific separations of radionuclides (Ludwig & Nguyen (2002) Sensors, 2, 397-416).

Calixarenes without a crown ether group have been proposed by Harris (Harris, McKervey, Svehla, & Diamond (1992) EP 0490631 A, U.S. Pat. No. 5,132,345) for the analytical determination of the alkali metal ions $Na^+$ and $K^+$ by means of ion sensitive electrodes. Even though the group of calixarene derivatives (2) disclosed in this patent document is very broad, it does not include compounds in which a phenyl ring points in the opposite direction and the carbonyl groups at the same time bear different substituents, as is shown in (2) for a cone conformation. The corresponding structure (3) is referred to as a partial cone conformation.

ervey, Böhmer, Vierengel, Tabatani, & Ferguson (1991) Workshop on Calixarenes and Related Compounds, Mainz 28.-30.8., p. 6). The compounds in question here are tert-butylcalixarenes in the cone conformation. Compounds having this structure can serve as starting materials for further derivatives having ionophoric properties (Ludwig, Tachimori, & Yamato (1998) Nukleonika, 43(2), 161-174).

Grady et al. (Grady, Cadogan, McKittrick, Harris, Diamond, & McKervey (1996) Analyt. Chimica Acta, 336, 1-12) report the utility of monocarboxylates of tert-butylcalix[4] arenes in ion-sensitive electrodes for $Na^+$. Here too, the compound in question is the cone conformer. No improvement in the selectivity for $Na^+$ compared to the ester precursor is observed.

A method patent by Reinhoudt (Reinhoudt, D. N., Engbersen, J. F. J., Peters, F. G. A. (2000) WO 2000029337, 25, May) is likewise directed at $Na^+$. Here, a calix[4]arene having 4 ester groups (Arnaud-Neu, Collins, Deasy, Ferguson, Harris,

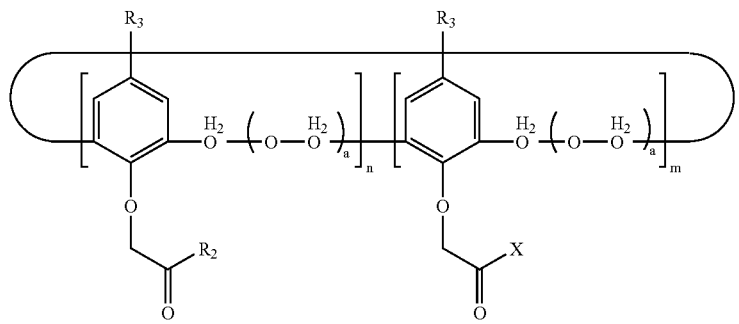

(2) according to EP 0490631

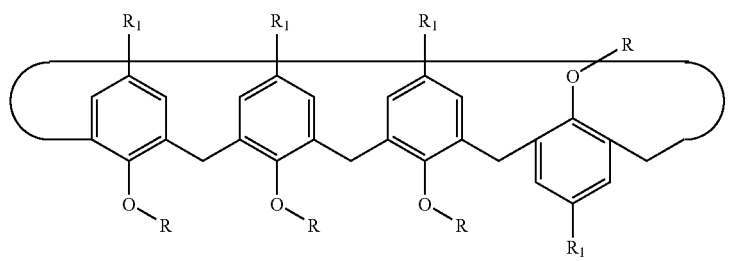

Partial cone conformation in the structure (3), R and R1 can vary within the molecule.

Calix[4]arenes without a cation-exchanging group have likewise been proposed by Harris et al. for analytical purposes (Cadogan, Diamond, Smyth, Deasy, McKervey, & Harris (1989) Analyst, 114 (Dec.), 1551-1554). A summary of ionophoric properties of calix[4]arenes may be found in a melting part work (McKervey, Schwing-Weill, & Arnaud-Neu (1996) Molecular Recognition: Receptors for Cationic Guests. Comprehensive Supramolecular Chemistry, ed. G. W. Gokel, Pergamon Press, New York, Oxford, vol. 1, 537-603).

Introduction of a single carboxylic acid group into calix[4] arene was achieved for the first time in one synthesis step by (Barrett, Böhmer, Ferguson, Gallagher, Harris, Leonard, et al. (1992) J. Chem. Soc., Perkin Trans. II, (9), 1595-1601; Böhmer, Vogt, Harris, Leonard, Collins, Deasy, et al. (1990) J. Chem. Soc, Perkin Trans. I, (2), 431-432; Owens, McK- Kaitner, et al. (1989) J. Amer. Chem. Soc., 111(23), 8681-8691; Chang & Cho (1986) J. Chem. Soc., Perkin Trans I, (2), 211-214; Kimura, Matsuo, & Shono (1988) Chem. Letters, (4), 615-616) or a COOH group (Barrett, et al. (1992) J. Chem. Soc., Perkin Trans. II, (9), 1595-1601; Böhmer, et al. (1990) J. Chem. Soc., Perkin Trans. I, (2), 431-432), which are known for their $Na^+$ selectivity, is proposed for removing $Na^+$ not taken up by plants from the circulating water of Dutch greenhouses by means of membrane methods. Its method is aimed at the removal of the $Na^+$ which is harmful to plants with selectivity over $K^+$, as the partition data demonstrate.

Calix[4]arenes can undergo additional interactions with heavy metal ions such as $K^+$ and $Cs^+$. These interactions are based on participation of the aromatic π systems and are referred to as cation-π interactions (Casnati (1997) Gazz. Chim. Ital., 127(11), 637-649; Inokuchi, Miyahara, Inazu, & Shinkai (1995) Angew. Chemie, 107(12), 1459-1461; Iwamoto, Araki, & Shinkai (1991) J. Org. Chem., 56(16), 4955-4962; Iwamoto, Fujimoto, Matsuda, & Shinkai (1990) Tetr. Lett., 31(49), 7169-7172). This is observed for conformers in an alternating or partial cone conformation. Nothing is said about a combination with a —COOH group or use for chemical separations involving $K^+$.

It is an object of the invention to remedy the disadvantages of the previously proposed solutions and to bind and extract both $K^+$ and $Na^+$ together and with high selectivity, in particular over ammonium ions, and to do this inexpensively.

This object has surprisingly been achieved by hydrophobic calix[4]arenes in a partial cone conformation which contain at least one cation-exchanging group. The invention therefore provides calix[4]arenes which, (i) contain at least one cation-exchanging group such as —COOH, (ii) are completely insoluble in water and can be used as extractants and (iii) have an unsymmetrical conformation. In addition, alpha-halogenated carboxylic acid groups can be present in the molecule. The calix[4]arenes of the invention can bind alkali metal ions and display selectivity for alkali metal ions over ammonium ions.

The advantages of the compounds of the invention are, inter alia, that:
1) In the preparation, time is saved compared to the crowned calixarenes as a result of the short reaction times and the simple work-up.
2) Inexpensive chemicals can be used in the preparation and the purification, as a result of which the costs are considerably reduced compared to the crowned calixarenes which require oligoethylene glycol ditosylates.
3) Secondary constituents such as $K^+$ and $Na^+$ can be separated off from main constituents by means of the compound corresponding to the structure (4). In contrast, conventional extraction or adsorption processes are based on separating off the main constituent in the purification step. The novel process therefore conserves resources.

The calixarenes of the invention have the following structure (4):

$R_4$=substituted or unsubstituted alkyl, aryl, alkylaryl, alkenyl, alkynyl group, preferably a hydrophobic but sterically small group, e.g. ethyl, methyl, propyl.

BRIEF DESCRIPTION OF THE DRAWINGS

The invention will now be described with reference to the drawings, wherein:

FIG. 1 shows the structure determined by means of X-ray structure analysis for $R_1$=tert-octyl (1,1,3,3-tetramethylbutyl) and $R_2$=$R_3$=H. In FIG. 1, the carbon atoms are shown in black and the oxygen atoms are shown in grey; hydrogen atoms are not shown.

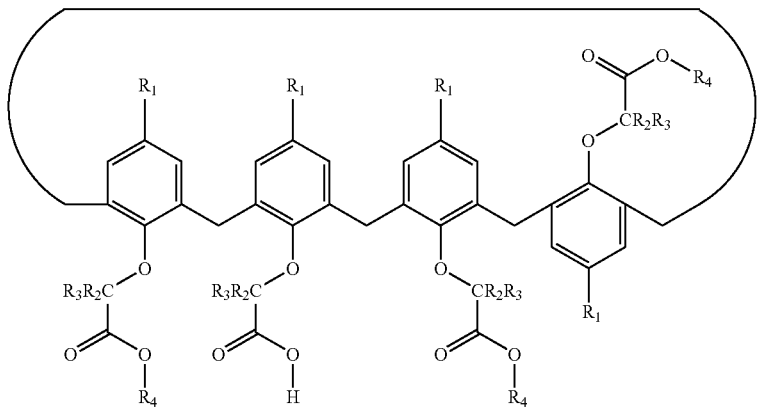

$R_1$=H, alkyl, aryl, arylalkyl, preferably branched alkyl groups, e.g. tert-butyl, tert-octyl;

$R_2$, $R_2$=H, alkyl, alkylaryl, halogen, preferably sterically small groups, e.g. H, F;

where $R_2$ can be identical to or different from $R_3$, e.g. $R_2$=$R_3$=H or $R_2$=Cl, $R_3$=H;

The calixarenes of the invention complex $K^+$ at the same time as $Na^+$, even in the simultaneous presence of an excess of $NH_4^+/NH_3$.

These properties can be explained, without thereby restricting the scope of the present invention, by means of the following structural features:

A calix[4]arene skeleton having a hollow space diameter similar to the diameter of the alkali metal ions $Na^+$, $K^+$.

A sufficient number of oxygen atoms to satisfy the coordination number and geometry of the alkali metal ions.

A partial cone conformation which makes it possible for $K^+$ with its unoccupied $^3d$ orbitals but not $NH_4^+$ to additionally undergo stabilizing cation-π interactions and thereby stabilize the complex.

A single cation-exchanging group which can be a carboxylic acid group or an alpha-halogenated carboxylic acid group and balances the charge of the alkali metal ion on complexation.

A hydrophobic molecular skeleton which gives the compound the following properties which are advantageous for chemical separations: (i) insolubility in water, (ii) solubility in organic diluents or good adhesion to porous organic support materials, (iii) good phase coalescence in extraction or membrane processes.

The compounds of the invention are compatible with other compounds such as commercial extractants or other calixarenes and can be combined with these for the purposes of chemical separations.

Figure 2:
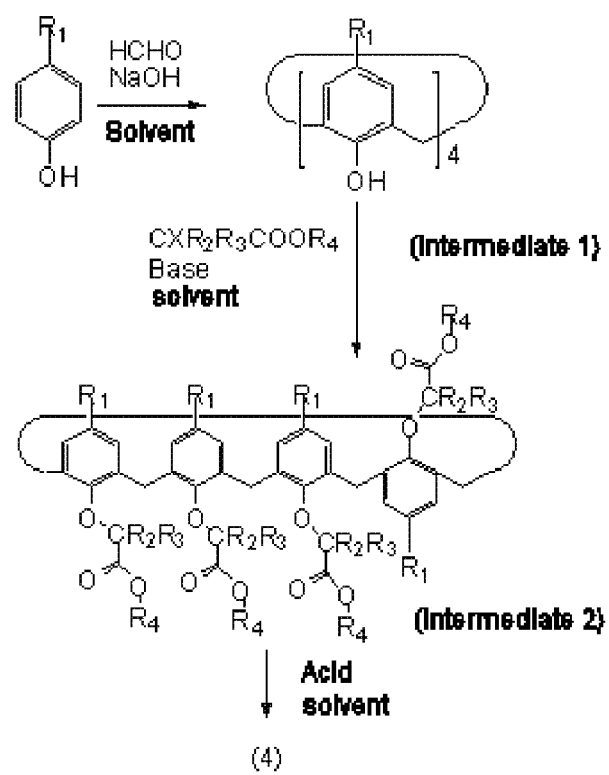
FIG. 2 shows the reactions scheme for the synthesis of a calixarene of structure (4). In the first step a para-substituted phenol is condensed with formaldehyde in catalytic amounts of NaOH in a solvent to intermediate 1. Intermediate 1 is reacted in the second step in the presence of base and alkyl acetate chlorinated or brominated in the 1-position in an inert solvent to intermediate 2. The derivative prepared in this way, intermediate 2, is reacted in the third step in a solvent with an acid to obtain the pure product having the structure (4). For further details regarding test conditions see example 2.

The novel compounds of the structure (4) can surprisingly be obtained in a single fashion by the following process, which is likewise subject matter of the invention:

In the process of the invention for preparing the calix[4]arenes,

A—A para-substituted phenol, preferably one having a branch in the para group, preferably tert-butylphenol or tert-octylphenol, is condensed with formaldehyde or paraformaldehyde in catalytic amounts of NaOH in a high-boiling inert solvent, preferably one which has a boiling point in the range 200-260° C. and is capable of forming an azeotrope with the water of reaction, e.g. petroleum ether or diphenyl ether, to form the calix[4]arene (FIG. 2). These compounds, hereinafter referred to as intermediate 1, have been known as basic science for a number of decades (Gutsche (1989) *Calixarenes*, (1998) *Calixarenes Revisited*, The Royal Society of Chemistry, Cambridge, UK, Schwetlick (2001) *Organikum*, Wiley-VCH).

B—This intermediate is reacted in the presence of an excess of a base, preferably a strong base having a $pK_B<3$ and particularly preferably a strong base having a template effect, e.g. KOalkyl, e.g. KO′Bu or KO″Bu with singly or multiply halogenated alkali acetates, preferably alkyl acetates chlorinated or brominated in the 1-position, in an inert solvent of one of the following classes, without being restricted to this listing, at temperatures from −10 to +150° C., preferably from 10 to 50° C., for one day. As solvents, it is possible to use substituted and unsubstituted ethers, alkanes, cycloalkanes, aromatics, heterocycles, carboxamides, nitriles, preferably ones having a high solvent capability for the reactants, e.g. tetrahydrofuran. The first derivative obtained in this way can be freed of residual salts by washing with dilute hydrochloric acid and purified by recrystallization from an inert solvent, preferably an alcohol such as ethanol.

C—The derivative prepared in this way according to B, intermediate 2, is reacted in an inert organic solvent, preferably one having a high solvent capability for the starting materials, e.g. tetrahydrofuran, alcohol, chloroform, with a large excess of an acid, preferably a strong acid, e.g. hydrochloric acid or trifluoroacetic acid, at temperatures of from −10 to +150° C., preferably from 20 to 40° C., for one day. After washing with water, the pure product having the structure (4) is obtained. The product is capable of selectively removing $K^+$ and $Na^+$ from aqueous solutions. If the product is to be used for removal from strongly acidic aqueous phases, $R_2$ or $R_3$ or $R_2$ and $R_3$ is/are a halogen, preferably F or Cl.

In the case of the calix[4]arenes described here, the synthesis surprisingly leads, presumably as a result of template effects, to the derivatives having the desired structure in high reaction yields.

These template effects can, without thereby restricting the scope of the present invention, be explained as follows:

The first, surprising template effect is presumably brought about by the organic-soluble $K^+$-containing strong base, e.g. KO′Bu, in the first derivative formation step and fixes the molecule in the desired conformation. When $R_1$=tert-octyl, this is the first published structure in partial cone conformation. Its preparation under the reaction conditions known hitherto for $R_1$=tert-butyl is possible only in reaction yields of less than 2% of theory if at all, as our own preliminary tests have shown.

Figure 1:
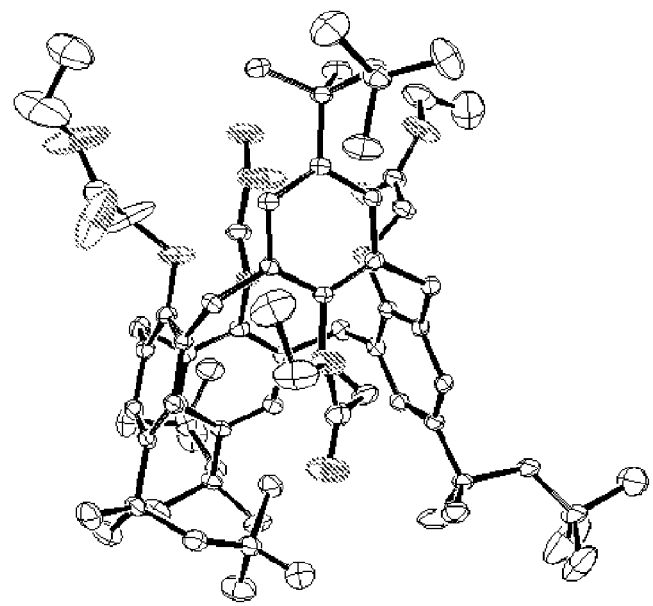
FIG. 1 shows the results of X-ray structure analyses on calixarenes of structure (4) for $R_1$=tert-octyl (1,1,3,3-tetramethylbutyl), $R_2$=$R_3$=H, and $R_4$=$C_2H_5$. Carbon atoms are shown in black and oxygen atoms are shown in grey; hydrogen atoms are not shown.

The second, likewise surprising template effect occurs when the product of the first synthesis step is heated with an about 20-fold molar excess of acid. As the crystal structure in FIG. 1 and the nuclear resonance data (vide infra) show, only the middle one of the three adjacent ester groups is hydrolytically cleaved. In contrast thereto, partial hydrolysis of the cone conformer is achieved even with equimolar amounts of acid (Böhmer, et al. (1990) J. Chem. Soc., Perkin Trans I, (2), 431-432).

The compounds of the invention are extraordinarily chemically stable, which is reflected in the fact that they can be circulated in an extraction/backextraction cycle a number of times under alkaline (pH≦11) or acidic conditions without impairment of the separating action, as could be shown by means of the nuclear resonance spectra. The compounds are nontoxic and completely insoluble in the aqueous phase. They are solids which do not burn readily and can be stored for an unlimited time.

In use, the compound having the structure (4) either alone or in admixture with further extractants or adsorption media is dissolved in a chemically inert organic diluent, preferably one having a low vapor pressure, e.g. high-boiling aliphatics, or chemically or adsorptively bound to a porous support, preferably by occupation of the surface of macroporous structures such as polymers.

In contact with an aqueous solution which in addition to $K^+$ and $Na^+$ can also contain a large excess of salts of other metals, of ammonium, of other bases or of acids and also of uncharged organic compounds, the compound highly selectively extracts the alkali metal ions $K^+$ and $Na^+$ and leaves the other materials in the aqueous phase. The alkali metal ions are removed from the laden organic phase or the laden adsorbent in a few minutes by bringing the organic phase or adsorbent into contact with acid, preferably a dilute solution of a strong acid, e.g. 0.1 M sulfuric acid, regardless of the temperature. Here, the extractant is converted into the original, uncomplexed form and is available for a fresh cycle.

The possible applications of such separations are:

1) Removal of $K^+$ and $Na^+$ from process water containing a material of value. The material of value can be precipitated from the purified aqueous solution and has a high purity.
2) Removal of $K^+$ and $Na^+$ from circulating water in production processes in which $K^+$ and $Na^+$ accumulate. If the complexing agent is fixed on a solid support or a copolymer is prepared using the complexing agent or the complexing agent is used directly as a solid, the chemical properties are retained and removal of $K^+$ and $Na^+$ takes place.
3) Simultaneous removal of all undesirable impurities including $K^+$ and $Na^+$ from aqueous solutions by use of a mixture of at least one compound according to the invention with other extractants or adsorption media. The capability of binding $K^+$ and $Na^+$ is surprisingly retained even in a mixture with other compounds which remove further materials from the aqueous phase.

4) The quantitative analytical determination of the content of $K^+$ and $Na^+$ in ammoniacal solutions when at least one compound according to the invention is used in conjunction with a sensor. The selective complexation makes it possible for the content of the alkali metal ions $K^+$ and $Na^+$ to be determined quantitatively in ammoniacal solutions when a compound according to the invention is used as part of a sensor. A sensor can be, for example, an ion-sensitive electrode, a modified field effect transistor or an optode.

5) The removal of $Na^+$ and $K^+$ from aqueous solutions and the masking of them, so that undesirable secondary effects can no longer occur. The compounds of the invention complex and bind $K^+$ and $Na^+$ selectively over ammonium ions, other cations, anions and uncharged compounds. This selectivity can be exploited for removal by means of liquid-liquid extraction.

The invention is illustrated by an example without being restricted to this example:

EXAMPLES

1.) Preparation

For the preparation of (4) with $R_1$=tert-octyl, $R_2$=$R_3$=H and $R_4$=$C_2H_5$, the following synthesis conditions were employed:

10 gram of tert-octylcalix[4]arene (Cornforth, D'Arcy Hart, Nicholls, Rees, & Stock (1955) Brit. J. Pharmacol., 10, 73-86; Ohto, Yano, Inoue, Yamamoto, Goto, Nakashio, et al. (1995) Analyt. Sciences, 11, 893-902) are heated with 13 gram of potassium tert-butoxide in 150 milliliters of dried tetrahydrofuran under reflux for 4 hours. About 9 milliliters of ethyl bromoacetates are then added dropwise while stirring. The mixture is stirred for about 1 day.

Instead of THF, it is possible to use other inert solvents such as petroleum ether. Reaction-accelerating additives such as KI can be mixed in at the beginning. If $K_2CO_3$ (3 gram) is additionally added at the beginning, a cone isomer is formed as by-product in a yield of about 10% and crystallizes out together with the main product.

It is possible to use ethyl chloroacetate in place of ethyl bromoacetate, in which case the reaction mixture is subsequently heated to about 50° C.

The reaction mixture is quenched by addition of 50 milliliters of water and extracted with 25 milliliters of $CH_2Cl_2$. The organic phase is washed a number of times with about 0.5 molar HCl and is crystallized by addition of about 25 milliliters of ethanol.

The filtered and dried precipitate (11 gram) is dissolved in about 20 milliliters of $CHCl_3$ and heated gently in 11 milliliters of trifluoroacetic acid for 12 hours while stirring. The organic phase is then washed a number of times with water until it is neutral. The solvent is taken off and the product remains as a resinous, slightly yellowish composition which softens on heating.

Instead of $CHCl_3$, it is also possible to use another solvent such as $CH_2Cl_2$, tetrahydrofuran or alcohol. It is also possible to use another medium strength to strong non-oxidizing acid in place of trifluoroacetic acid. The acid concentration in the organic phase has to be sufficiently high. If, for example, an aqueous solution of HCl is used, a water-soluble organic solvent such as tetrahydrofuran then has to be used for the work-up.

2.) Identification

The products were confirmed by means of their NMR spectra, crystal structure analysis (vide supra), mass spectra and chromatograms:

Ester derivative with $R_1$=tert-octyl, $R_2$=$R_3$=H, $R_4$=$C_2H_5$: $^1H$ NMR, δ (ppm, $CDCl_3$/TMS)=0.64 (s, 18H), 0.78 (s, 9H), 0.81 (s, 9H), 0.97 (s, 6H), 1.14 (t, 9H), 1.28 (t, 9H), 1.34 (t, 6H), 1.46 (m, 10H), 1.72 (s, 2H), 1.78 (s, 2H), 3.11 (d, 2H), 3.85 (s, 4H), 3.98 (q, 2H), 4.2-4.34 (m, 14H), 4.43 (d, 2H), 4.48 (d, 2H), 6.45 (s, 2H), 7.02 (s, 4H), 7.32 (s, 2H);

$^{13}C$ NMR, δ (ppm, $CDCl_3$/TMS)=$C_{CH_3}$ and Ar—$CH_2$—Ar: 13.79, 14.04, 27.92, 30.41-32.59 (m), 36.67, 37.50, 37.66, 37.76, $C_{CH_2}$: 56.57, 57.38, 57.58, 59.22, 59.91, 60.28, 60.36, 67.59, 70.13, 71.19, $C_{Ar}$: 126.25, 126.64, 128.92, 130.88, 131.04, 131.65, 132.92, 134.73, 143.04, 143.18, 143.59, 152.13, 153.83, 154.83, $C_{CO}$: 168.87, 168.99, 170.84;

Elemental analysis: $C_{76}H_{112}O_{12}$, calculated C, 75.0%, H, 9.3%. found C, 74.8%, H, 9.06%.

m.p. (Gallenkamp): 155° C., DSC (Netzsch DSC 200 calorimeter, $N_2$, 10K/min) 149.7° C. (43.2 J/g);

MS (FAB$^+$, 3 kV, xenon, matrix MNBA) m/e=1218 [L+H]$^+$, 1240 [L+Na]$^+$,

DC ($SiO_2$, $CHCl_3$/EtOH 9:1) $R_f$=0.7 (for comparison: cone conformer $R_f$=0.4, starting material $R_f$=0.95);

Compound (4) with $R_1$=tert-octyl, $R_2$=$R_3$=H, $R_4$=$C_2H_5$: $^1H$ NMR, δ (ppm, $CDCl_3$/TMS)=0.38 (s, 15H), 0.57 (s) and 0.62 (s) and 0.67 (s) (21H), 1.0-1.1 (m, 21H), 1.25-1.45 (m, 16H), 1.61 (s, 4H), 3.02 (d, 2H), 3.47 (s, 1H), 3.73 (d, 2H), 3.87-4.07 (m, 11H), 4.32 (s, 2H), 4.62 (d, 2H), 4.70 (d, 2H), 6.74 (s, 2H), 6.92 (s, 2H), 7.02 (s, 2H), 7.16 (s, 2H);

Elemental analysis:, $C_{74}H_{108}O_{12}$, calculated C, 74.7%, H, 9.15%. found C 74.3%, H 8.85%.

m.p.: softens above 40° C.;

MS (FAB$^-$, 3 kV, xenon, matrix MNBA) m/e=1188 [L−H]$^-$; (FAB$^+$) m/e=1212 [L+Na]$^+$;

DC ($SiO_2$, $CHCl_3$/EtOH 9:1) Rf=0.

3.) Use

Figure 3:
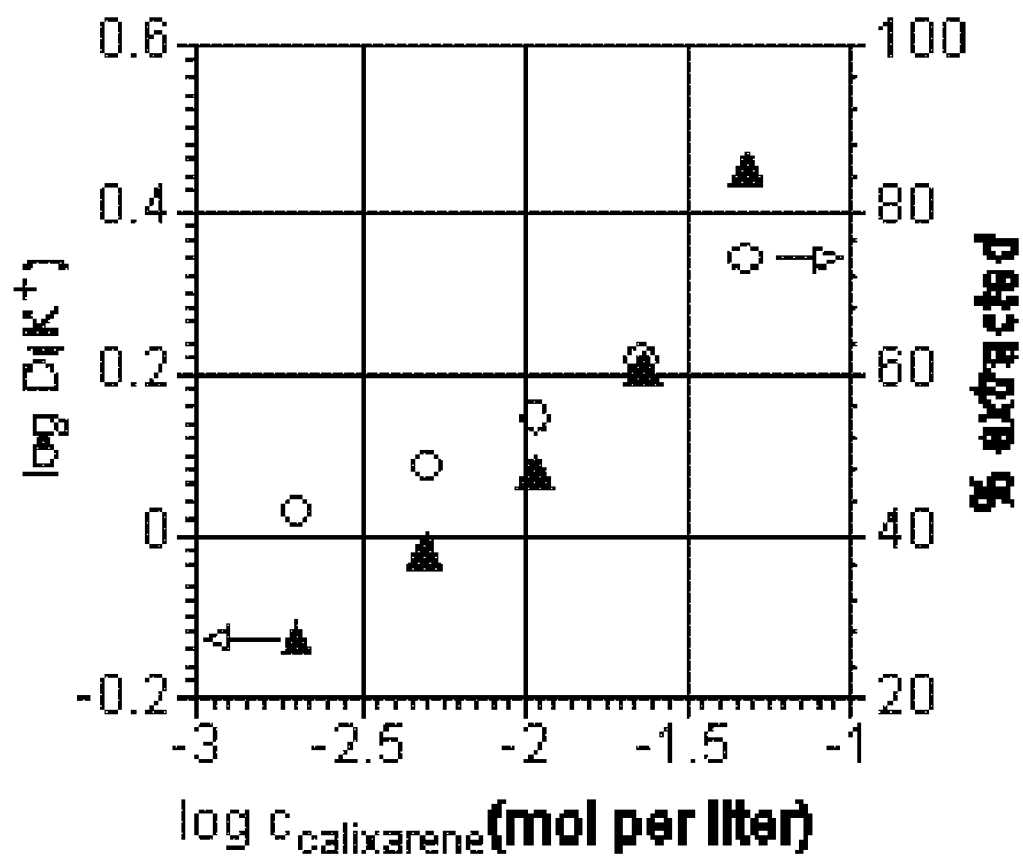
FIG. 3 shows the results of a liquid-liquid (chloroform-water) extraction of $K^+$ ions by means of calixarene of structure (4) for $R_1$=tert-octyl, $R_2$=$R_3$=H, and $R_4$=$C_2H_5$ as extraction agent. The logarithms of the partition coefficients D of $K^+$ (closed symbols) in single-stage extractions from strongly ammonium-containing solution and the percentage of extracted K+ (open symbols) are plotted against different concentrations of extraction agent. (D=concentration of $K^+$ in the organic phase/concentration of $K^+$ in the aqueous phase). For further details regarding test conditions see example 3.

In the case of (4) and $R_1$=tert-octyl, $R_2$=$R_3$=H, $R_4$=$C_2H_5$, the partition coefficients D (D=concentration of metal in the organic phase/concentration of metal in the aqueous phase) shown in FIG. 3 are obtained in the liquid-liquid extraction.

FIG. 3: Logarithm of the partition coefficients of $K^+$ in single-stage extraction from strongly ammonium-containing solution using different concentrations of (4) with $R_1$=tert-octyl, $R_2$=$R_3$=H, $R_4$=$C_2H_5$ in $CHCl_3$. Closed symbols: log D, open symbols: % of extracted $K^+$.

Experimental conditions: solution of ligand (4) in chloroform, 0.5 mol/liter of $NH_4Cl/NH_3$ buffer (pH 10), 200 ppm of $K^+$ before extraction, analysis: FES.

The extraction yield can be increased in a simple fashion by increasing the ligand concentration. The reduction in concentration of $K^+$ by 50% and more in a single-stage extraction/reextraction allows effective separation.

The invention claimed is:

1. A calix[4]arene having a partial cone formation and having the structure of the formula (4):

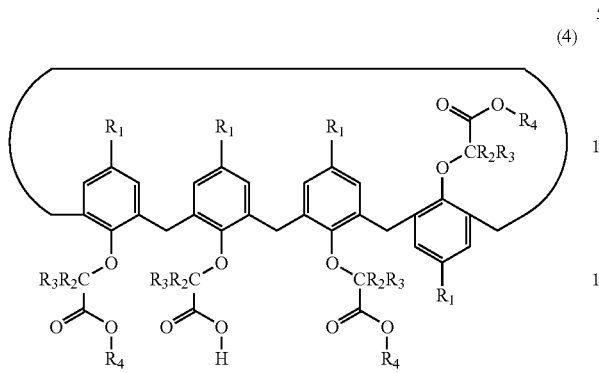

(4)

where
R₁ is H, or an alkyl, aryl or arylalkyl group,
R₂ is H, F, Cl,
R₃ is H, F, Cl, and
R₄ is a substituted or unsubstituted alkyl, alkenyl, aryl or arylalkyl group.

2. The calix[4]arene as claimed in claim 1, which is a compound of the structure (4) in which
$R_1$=tert-butyl, $R_2$=$R_3$=H, $R_4$=$C_2H_5$;
$R_1$=tert-octyl, $R_2$=$R_3$=H, $R_4$=$C_2H_5$;
$R_1$=H, $R_2$=$R_3$=H, $R_4$=$C_2H_5$;
$R_1$=tert-butyl, $R_2$=$R_3$=H, $R_4$=$CH_3$;
$R_1$=tert-octyl, $R_2$=$R_3$=H, $R_4$=$CH_3$;
$R_1$H, $R_2$=$R_3$=H, $R_4$=$CH_3$;
$R_1$=tert-butyl, $R_2$=$R_3$=Cl, $R_4$=$C_2H_5$;
$R_1$=tert-octyl, $R_2$=$R_3$=Cl, $R_4$=$C_2H_5$;
$R_1$=H, $R_2$=$R_3$=Cl, $R_4$=$C_2H_5$;
$R_1$=tert-butyl, $R_2$=H, $R_3$=F, $R_4$=$C_2H_5$;
$R_1$=tert-octyl, $R_2$=H, $R_3$=F, $R_4$=$C_2H_5$; or
$R_1$=H, $R_2$=H, $R_3$=F, $R_4$=$C_2H_5$.

3. A process for preparing a calix[4]arene of the formula (4) as claimed in claim 1, comprising the following steps:
a) reacting a calix[4]arene of intermediate 1:

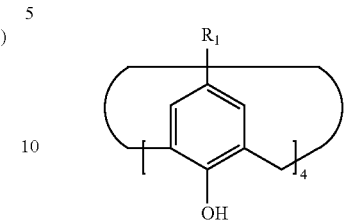

where $R_1$ is H, or an alkyl, aryl or arylalkyl group,
using a soluble strong base which does not contain an OH group and a reagent of the formula
$CXR_2R_3COOR_4$
where X=Br, Cl, I; $R_2$ is H, F, Cl; $R_3$ is H, F, Cl; and $R_4$ is a substituted or unsubstituted alkyl, alkenyl, aryl or arylalkyl group,
in a water-free organic solvent with heating and, optionally, purification by crystallization; and
b) reacting the product of step a) with a medium strength to strong acid in an aqueous-organic medium to form the compound of the formula (4).

4. A method of binding the alkali metal ions $K^+$ and $Na^+$ comprising contacting the alkali metal ions with a calix[4]arene as claimed in claim 1.

5. The method as claimed in claim 4, which comprises extraction of the alkali metal ions $K^+$ and $Na^+$.

6. The method as claimed in claimed 4, which comprises adsorption of $K^+$ and $Na^+$.

7. The method as claimed in claim 4, which comprises contacting the alkali metal ions with a calix[4]arene in admixture with other extractants or adsorption media.

8. The method as claimed in claim 4, which further comprises determining the content of $K^+$ and $Na^+$.

* * * * *

UNITED STATES PATENT AND TRADEMARK OFFICE
CERTIFICATE OF CORRECTION

PATENT NO. : 7,393,969 B2  
APPLICATION NO. : 11/574144  
DATED : July 1, 2008  
INVENTOR(S) : Traving et al.

Page 1 of 1

It is certified that error appears in the above-identified patent and that said Letters Patent is hereby corrected as shown below:

In the Specification

Column 5, line 61, "$R_1$– II" should read -- $R_1 =H$ --

Column 8, line 14, "$R_1$– tert-octyl," should read -- $R_1=$ tert-octyl, --

Column 8, line 31, "(pH$\leqq$ 11" should read -- pH$\leq$ 11 --

Column 9, line 56, "CIICl$_3$" should read -- $CHCl_3$ --

Column 10, line 10, "– 0.64" should read -- =0.64 --

Column 10, line 37, "1.25 – 1.45 (m,16II), 1.61 (s, 4II), 3.02 (d,2II), 3.47 s,1II)," should read -- 1.25 – 1.45 (m,16H), 1.61 (s, 4H), 3.02 (d, 2H), 3.47 s,1H)," --

Column 10, line 58, "$R_2 – R_3$ – II, $R_4 – C_2II_5$ in CIICl$_3$" should read -- $R_2 = R_3 = H, R_4 = C_2 H_5$ in $CHCl_3$ --

In the Claims

Column 11, line 29, "$R_1$– tert-octyl," should read -- $R_1=$ tert-octyl, --

Column 11, line 33, "$R_1$ H" should read -- $R_1 =H$ --

Column 11, line 38, "$R_2$ – II," should read -- $R_2 =H,$ --

Signed and Sealed this  
Eleventh Day of February, 2014

Michelle K. Lee  
*Deputy Director of the United States Patent and Trademark Office*